United States Patent
Kahlman et al.

(10) Patent No.: US 10,265,006 B2
(45) Date of Patent: Apr. 23, 2019

(54) SENSOR FOR DETERMINING GAS CONCENTRATION

(71) Applicant: KONINKLIJKE PHILIPS N.V., Eindhoven (NL)

(72) Inventors: Josephus Arnoldus Henricus Maria Kahlman, Tilburg (NL); Hans Willem Van Kesteren, Eindhoven (NL); Nicolaas Lambert, Waalre (NL); Theodorus Petrus Henricus Gerardus Jansen, Deurne (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 921 days.

(21) Appl. No.: 14/760,366

(22) PCT Filed: Dec. 30, 2013

(86) PCT No.: PCT/IB2013/061409
§ 371 (c)(1),
(2) Date: Jul. 10, 2015

(87) PCT Pub. No.: WO2014/111779
PCT Pub. Date: Jul. 24, 2014

(65) Prior Publication Data
US 2016/0007894 A1 Jan. 14, 2016

Related U.S. Application Data

(60) Provisional application No. 61/753,048, filed on Jan. 16, 2013.

(51) Int. Cl.
*A61B 5/00* (2006.01)
*A61B 5/1455* (2006.01)
(Continued)

(52) U.S. Cl.
CPC ........ *A61B 5/14552* (2013.01); *A61B 5/1491* (2013.01); *A61B 5/6833* (2013.01);
(Continued)

(58) Field of Classification Search
CPC .............. A61B 5/1455; A61B 5/14551; A61B 5/14552; A61B 5/6833; A61B 5/1491; A61B 5/14556
See application file for complete search history.

(56) References Cited

U.S. PATENT DOCUMENTS 5,593,899 A 1/1997 Wilson et al.
2001/0034479 A1 10/2001 Ring et al.
(Continued)

FOREIGN PATENT DOCUMENTS

CN 1083734 A 8/1993
CN 2299329 Y 12/1998
(Continued)

OTHER PUBLICATIONS

Zakharov et al, "A Wearable Diffuse Reflectance Sensor for Continuous Monitoring of Cutaneous Blood Content", Physics in Medicine and Biology, vol. 54, No. 17, 2009, pp. 1-23.

*Primary Examiner* — Eric Winakur
*Assistant Examiner* — Chu Chuan (JJ) Liu
(74) *Attorney, Agent, or Firm* — Michael W. Haas

(57) ABSTRACT

The present invention provides an optical sensor unit (10) for measuring gas concentration, comprising: sensor means (12, 13) and first thermal insulation means (14, 16) at least partially surrounding said sensor means (12, 13). The sensor means (12,13) includes at least one sensing layer (12) adapted to be irradiated with a predetermined radiation (100), and at least one gas-permeable layer (13) adjacent to one side of the at least one sensing layer (12) and adapted to pass gas, which concentration is to be measured, through the (Continued)

gas-permeable layer (13) towards the at least one sensing layer (12). The optical sensor unit (10) is adapted to measure an optical response of the at least one sensing layer (12), which optical response depends on the gas concentration.

20 Claims, 7 Drawing Sheets

(51) Int. Cl.
*A61B 5/1491* (2006.01)
*G01N 21/59* (2006.01)
*G01N 33/00* (2006.01)

(52) U.S. Cl.
CPC ........... *G01N 21/59* (2013.01); *G01N 33/004* (2013.01); *A61B 5/14556* (2013.01); *G01N 2201/062* (2013.01)

(56) References Cited

U.S. PATENT DOCUMENTS

| | | |
|---|---|---|
| 2002/0092525 A1 | 7/2002 | Rump et al. |
| 2007/0054551 A1* | 3/2007 | Malagrino, Jr. ..... H01R 13/645 |
| | | 439/607.01 |
| 2011/0264001 A1 | 10/2011 | Cheung et al. |
| 2013/0053654 A1* | 2/2013 | Caduff ................. A61B 5/1455 |
| | | 600/301 |

FOREIGN PATENT DOCUMENTS

| | | |
|---|---|---|
| JP | S5588749 A | 12/1978 |
| JP | S5588750 A | 7/1980 |
| WO | 2010116297 A1 | 10/2010 |
| WO | 2012045047 A2 | 4/2012 |
| WO | 2012112222 A1 | 8/2012 |

* cited by examiner

SENSOR FOR DETERMINING GAS CONCENTRATION

CROSS-REFERENCE TO PRIOR APPLICATIONS

This application is the U.S. National Phase application under 35 U.S.C. § 371 of International Application Serial No. PCT/IB2013/061409, filed on Dec. 30, 2013, which claims the benefit of U.S. Application Ser. No. 61/753,048, filed on Jan. 16, 2013. These applications are hereby incorporated by reference herein.

TECHNICAL FIELD

The present invention relates to a sensor and a method for determining gas concentration.

BACKGROUND OF THE INVENTION

Neuromuscular disease, chronic obstructive pulmonary disease (COPD) and obese hypoventilation patients often suffer from chronic respiratory failure. Said patients need regular treatment of their respiratory failure at home. Hypoxemic patients are treated by oxygen therapy (mostly without ventilator support), while treatment by Invasive Ventilation (IV) or Non Invasive Ventilation (NIV) with environmental air helps bringing the high carbon dioxide blood gas level of hypercapnic patients back to an acceptable level. The efficacy of the ventilation is checked by measuring the base-line and the trends in the arterial oxygen and carbon dioxide levels during nocturnal ventilation.

Arterial blood gas measurements form the golden standard. Before starting ventilation treatment at home, patients stay at the hospital to optimize ventilator settings and monitor arterial blood gas values. Depending on disease severity and stability, patients have to return more or less regularly to the hospital for checks. A respiratory nurse can also visit the patient at home to check the ventilator and to install equipment that enables non-invasive monitoring of blood gas partial pressures. At home, blood gas levels are monitored typically during a night and data are stored together with ventilator and respiratory data for later analysis at the hospital.

The state of the art in non-invasive blood oxygenation monitoring, is by measuring the arterial oxygen saturation, which relates to the partial oxygen pressure via the oxygen dissociation curve. Pulse oximetry (SpO2) is an optical method for non-invasive monitoring of arterial oxygen saturation in a patient and has become one of the most commonly used technologies in clinical practice. Pulse oximetry is a reasonably low cost technology and is easy to use. It is the preferred method for blood oxygenation monitoring at home.

The state of the art in non-invasive monitoring of the partial pressure of CO2 is by means of capnography or by transcutaneous CO2 (PtcCO2) monitoring. For intubated patients with a healthy lung the end-tidal CO2 (etCO2) value obtained by capnography offers a good indication of the arterial CO2 value. However, in case of non-invasive ventilation where air leaks between mask and face are usually present and the patients have severe respiratory diseases capnography is often not a reliable method. In most hospitals a combination is used of capnography for trend monitoring and analysis of an arterial blood sample to obtain an occasional accurate value.

Transcutaneous CO2 monitoring is not disrupted by airleaks and respiratory diseases but requires trained personal to obtain reliable values and shows some inaccuracy due to variation in skin properties among adults. At home non-invasive CO2 blood gas monitoring is less frequently used than oximetry despite its high relevance for patients receiving ventilation.

The current transcutaneous CO2 sensor is based on a 40 year old concept of
- a thermostatically controlled heater to increase blood perfusion and gas-permeability of the skin,
- a fluid layer between skin and sensor membrane,
- a gas-permeable membrane covering the sensor,
- an electrolyte solution between membrane and sensor,
- a sensor comprising an electrochemical pH sensor and reference electrode, and
- an algorithm to compensate for temperature effects and skin metabolism.

To derive the transcutaneous CO2 value from the measured—cutaneous—partial CO2 pressure, the difference between the sensor temperature and the arterial blood temperature of 37° C. has to be taken into account. Furthermore, an offset is subtracted from the measured value to compensate for the skin metabolism that varies somewhat with skin temperature.

Arterialization of the skin is essential for transcutaneous blood gas measurements to obtain a transcutaneous value that is close to the arterial CO2 blood gas level. The existing technology is based on arterialization by heating the skin below the sensor surface. In currently available transcutaneous systems the minimal sensor temperature for arterialization is 42° C. and the required heating power is ~500 mW at maximum, mainly needed to compensate for the cooling effect of the blood flow.

In order to come up with a low-cost, non-invasive PaCO2 monitoring solution chemo optical sensing technology has been applied for transcutaneous CO2 detection.

FIG. 1 shows a typical principle of operation of a chemo optical sensor for transcutaneous CO2 detection. A sensor spot with a gas-permeable layer 13 (e.g. silicone membrane+TiO2), which is transparent to gas and reflective to light, is in contact with a patient's skin. The gas-permeable layer 13 facilitates gas diffusion (e.g. CO2) from the skin into a sensing layer 12 (e.g. silicone membrane+reference dye+indicator dye), which is transparent to gas, incorporates an indicator dye which is pH sensitive and a reference dye which is insensitive to gas concentrations. An optically transparent carrier 11 covers the sensing layer 12. The optically transparent carrier 11 may have a thickness d1 of about 0.2 mm, the sensing layer 12 may have a thickness d2 of about 0.1 mm, and the gas-permeable layer 13 may have a thickness d3 of about 0.1 mm. A diameter of the sensor spot x1 may be about 5 mm.

A predetermined radiation 100 is irradiated onto the sensor spot and in particular the sensing layer 12. The predetermined radiation 100 may have a wavelength of about 470 nm (blue-green LED). The indicator and reference dye emit radiation 200 in response to an excitation caused by the predetermined radiation 100. The characteristics of said radiation 200 (optical response) depend on the amount of CO2 gas that is present in/has diffused into the sensing layer 12. Accordingly, by analyzing the radiation 200, a gas concentration in the sensing layer and thus, in the skin, can be determined.

At first sight the properties of these sensor spots look unmistakably advantageous for the design of a transcutaneous sensor device for the home market in terms of dynamic range, pre-calibration/compensation for deviating temperature, stability and cost-effectiveness.

In order to dissolve the polar indicator dye into the hydrophobic polymer sensing layer a lipophilic phase transfer agent is added, which lipophilic phase transfer agent also serves as an internal buffer to provide water for production of carbonic acid. However, the water content in the sensor spots is known (and experimentally validated) to display a strong cross-sensitivity towards osmotic differences, which makes the control of the osmotic properties of the surrounding fluid between tight constraints inevitable. This is well feasible in certain application fields of these sensor spots but is cumbersome or impossible for others. In theory, sensitivity to osmolality can be reduced at the cost of a trade-off on the shelf-life and response time of the sensor spots.

Furthermore, temperature affects the excited states and chemical balance inside the dye and shifts the detection curve. Luminescence changes due to variations in the light-path are effectively suppressed by using a Dual-Lifetime Referencing technology. By balancing the temperature sensitivity and photo-bleaching of the indicator- and reference-dye also these effects can be suppressed. In the end the sensor signal can be (partly) compensated by a-priori knowledge of the temperature coefficients.

As mentioned above, said $CO_2$ sensor spots are designed for in-fluid measurements where temperature and osmotic pressure is uniform. When shifting from this (intended) application towards a transcutaneous sensor an additional problem arises, namely:

A temperature gradient across the membrane of the sensor spot occurs, in particular in a direction perpendicular to the sensing plane, causing relevant gradient-dependent signal drift, most likely caused by fluid pumping and related osmotic changes. Generally speaking this phenomenon is known as thermal creep or thermal transpiration and was first utilized by M. H. Knudsen (1910) for gas pumping. It is also related to thermo phoresis and thermo diffusion. It is a new and highly relevant problem in chemo-optical sensor spots applied for transcutaneous sensing, as thermal gradients are inevitably present.

WO 2012/045047 discloses a non-invasive transcutaneous blood gas sensing system for determining information on arterial blood gas in a mammal, comprising a combined diffusion and measurement chamber comprising at least one gas permeable surface adapted to allow transcutaneous diffusion of analytes from a mammal when the gas permeable surface is in contact with the mammal, at least one optical chemical sensor positioned in the combined diffusion and measurement chamber that is adapted to chemically interact and/or physically react with a respective analyte, and an optoelectronic system positioned outside the combined diffusion and measurement chamber for remotely detecting the chemical interaction and/or the physical interaction of the at least one optical chemical sensor.

SUMMARY OF THE INVENTION

In view of the above disadvantages and problems associated with the prior art, it is an object of the present invention to provide an optical sensor unit for measuring gas concentration and a method using the same that allow a reliable and accurate measurement of said gas concentration.

This object is solved by the features of the independent claim.

The present invention is based on the idea to reduce temperature gradients in sensor means of the optical sensor unit. This is achieved by thermally insulating the sensor means from its environment and/or by actively reducing a thermal flux into the sensor means and/or by minimizing a thermal resistance of the sensor means. Accordingly, temperature gradients, for instance in a direction perpendicular and/or parallel to a sensing layer and/or a gas-permeable layer included in the sensor means, can be minimized or even eliminated, thereby preventing the gradient-dependent signal drift (thermal creep/thermal transpiration) associated with the prior art. Furthermore, by suppressing temperature gradients, temperature effects on the exited states and chemical balances inside the sensing layer (for instance a dye) are avoided, and hence, luminescence changes due to temperature are suppressed. This significantly increases reliability and accuracy of the gas concentration measurement.

According to one aspect of the present invention, an optical sensor unit for measuring gas concentration preferably comprises sensor means and first thermal insulation means at least partially surrounding said sensor means. Said sensor means includes at least one sensing layer adapted to be irradiated with a predetermined radiation, and at least one gas-permeable layer adjacent to one side of the at least one sensing layer and adapted to pass gas, which concentration is to be measured, through the gas-permeable layer towards the at least one sensing layer. The optical sensor unit is further adapted to measure an optical response of the at least one sensing layer, which optical response depends on the gas concentration. The first thermal insulation means at least partially surrounds the sensor means, wherein the term "surrounding" may comprise surrounding from any side, but may also comprise surrounding a lateral outer diameter side of the sensor means.

In an exemplary embodiment, when the optical sensor unit is attached to a patient's skin, gas from the skin, for instance oxygen ($O_2$) or carbon-dioxide ($CO_2$), passes the gas-permeable layer, which is in contact with the skin either directly or via a contact medium (gel), and diffuses into the sensing layer as long as the gas-partial pressure in the skin is higher than the gas-partial pressure in the sensor means. Gas will pass the permeable membrane into or out of the sensing layer until equilibrium is established. The sensing layer, which is irradiated, for instance with visible light, infrared light and/or ultraviolet (UV) light, generates luminescent light (optical response), the intensity of which is a function of time which depends on the current gas concentration in the sensing layer. Accordingly, e.g. a blood gas concentration of the patient can be calculated by using the gas concentration in the sensing layer obtained by measuring and analyzing the optical response (luminescent light).

Preferably, the optical sensor unit further comprises first heat conducting means at least partially surrounding the sensor means and/or the first thermal insulation means. The first heat conducting means may surround the sensor means at a lateral side thereof. In particular, the sensor means could be of disc shape or annular shape, and the first heat conducting means could be shaped as a hollow cylinder accommodating said sensor means. Moreover, the first heat conducting means is configured to contact a patient's skin in order to apply heat to the skin, thereby increasing blood perfusion and gas-permeability of the skin. The first heat conducting means is thermally isolated from the sensor means by the first thermal insulation means, so that no heat will flow from the first heat conducting means into the sensor means, thereby avoiding any temperature effect on the sensor means.

Preferably, the optical sensor unit further comprises at least one first heating device providing heat to the first heat conducting means. Providing heat to the first heat conducting means could be achieved by thermally coupling the first heat conducting means to the first heating device, wherein the latter might e.g. by a resistance heater. Alternatively, the first heating device may comprise at least one coil for inductively heating the first heat conducting means. In this case, the first heat conducting means could comprise metal or could e.g. be a metal washer. Moreover, the at least one first heating device is preferably detachably connected to the optical sensor unit. In particular, the sensor means and the thermal insulation means could be integrated into a one-way (disposable) device, wherein the first heating device could be reused. This reduces costs, since only certain components, that cannot be reused, are dumped (e.g. the sensor means), while other components, such as the first heating device, are reused.

Preferably, the optical sensor unit further comprises at least one radiation supplying means adapted to irradiate the at least one sensing layer with the predetermined radiation, and at least one radiation detection device adapted to detect the optical response of the at least one sensing layer. The at least one radiation supplying means and/or the at least one radiation detection device are preferably detachably connected to the optical sensor unit, and are preferably coupled to (or integrally formed with) the first heating device to form a reuseable unit.

The at least one radiation supplying means may be an active light source, such as an LED, and the at least one radiation detection device may be a photosensitive device. Alternatively, a light guiding structure may be used to irradiate the sensing layer with the predetermined radiation. The light guiding structure may be arranged above the sensing layer/an optically transparent layer covering the sensing layer, and may be connected via an optical fiber to a light source external to the optical sensor unit. Light from the external light source is guided through the optical fiber and introduced into the guide lighting structure, which is adapted to direct that light towards the at least one sensing layer. Further, the same light guiding structure may be used to collect the optical response of the sensing layer and to guide said optical response, for instance luminescent light, via the same or a different optical fiber to a device external to the optical sensor unit for analysis.

In a preferred embodiment, a combination of both alternatives is employed. In particular, an active light source included in the optical sensor unit could be used to irradiate the sensing layer with the predetermined radiation, wherein a light guiding structure could then be used to collect the optical response of the sensing layer and to guide the optical response, for instance said luminescent light, via at least one optical fiber to a device external to the optical sensor unit for analysis. Alternatively, the optical sensing unit may be adapted to perform said analysis. Preferably, the light is coupled into the sensing layer and luminescence light is collected through the same surface of the sensing layer.

Preferably, the at least one radiation supplying means, the at least one radiation detection device and the at least one first heating device form the reuseable unit. Accordingly, the remaining parts of the optical sensor unit, such as the sensor means (i.e. the sensing layer and the gas-permeable layer), the first thermal insulation means and/or the first heat conducting means may form a disposable unit. This saves costs, since expensive parts such as light sources and/or detection devices and/or electronics are reused.

Preferably, when the first heat conducting means is part of the disposable unit, the first heating device included in the reusable unit may comprises at least one coil for inductively heating the first heat conducting means. In this case, the first heat conducting means could comprise metal or could e.g. be a metal washer.

Preferably, the first heat conducting means as configured to at least partially cover a side of the at least one gas-permeable layer opposite the at least one sensing layer. The part of the first heat conducting means covering the at least one gas-permeable layer may be a perforated layer, that suppresses lateral thermal gradients across the sensor means, in particular the gas-permeable layer, and preferably also the sensing layer. Preferably, a thin metal sheet, perforated to allow, for instance, $CO_2$ exchange, is used. This allows a better definition of a temperature of the sensor means, which is beneficial for accuracy.

Preferably, the first heat conducting means comprises at least one extension part at least partially extending into the sensor means. For instance, the at least one extension part may be column-shaped and may extend from the part of the first heat conducting means covering the gas-permeable layer, and may penetrate into the sensor means. Preferably, said extension part penetrates at least the gas-permeable layer, and preferably also at least partially the sensing layer. This allows a better heat distribution inside the sensor means, thereby leading to reduced thermal gradients.

Preferably, the optical sensor unit further comprises second heat conducting means configured to at least partially cover a side of the at least one gas-permeable layer opposite the at least one sensing layer while being thermally isolated from the first heat conducting means. Accordingly, heat is uniformly distributed in the sensor means, in particular in a direction parallel to the plane of the gas-permeable membrane (or the sensing layer).

Preferably, at least a portion of the second heat conducting means covering the side of the at least one gas-permeable layer as perforations formed therein. This is similar to the above-mentioned case. In particular, the portion covering the side of the at least one gas-permeable layer may be a thin metal sheet, that is perforated to allow, for instance, $CO_2$ exchange, and, at a same time, heat is equally distributed horizontally across the gas-permeable membrane, in order to reduce thermal gradients for improving measurement accuracy.

Preferably, the second heat conducting means comprises an extending portion extending at least partially between the sensor means and the first thermal insulation means. The extending portion may be interposed between the sensor means and the first heat conducting means, so as to enable a uniform heat distribution in the sensor means while being thermally isolated from the first heat conducting means.

Preferably, the second heat conducting means comprises at least one extension part at least partially extending into the sensing means. This is identical to the above-described situation. In particular, the at least one extension part may be column-shaped and may extend from the part of the second heat conducting means covering the gas-permeable layer, and may penetrate into the sensor means. Preferably, said extension part penetrates at least the gas-permeable layer, and preferably also at least partially the sensing layer. This allows a better heat distribution inside the sensor means, thereby leading to reduces thermal gradients.

Preferably, the optical sensor unit further comprises second thermal insulation means configured to thermally isolate the first heating device from the at least one radiation supplying means and/or the at least one radiation detection device. In particular, the second thermal insulation means may be interposed between the first heating device and the radiation supplying means and/or the at least one radiation detection device, in order to avoid heat from being introduced from the first heating device into the radiation supplying means and the radiation detection device. Accordingly, temperature effects on the radiation supplying means and/or the radiation detection device are avoided, thereby increasing accuracy of said radiation supplying means and radiation detection device.

Preferably, the optical sensor unit further comprises at least one second heating device configured to heat the at least one radiation supplying means and/or the at least one radiation detection device while being thermally isolated from the first heating device by the second thermal insulation means. The second heating device may be used to keep a stable temperature of the radiation supplying means and the detection device, so that a detection accuracy and sensitivity is maintained. Furthermore, the at least one second heating device may be used to perform an active zero heat flux (ZHF) method. Thus, the second heating device may be controlled to heat the radiation detection device and/or the radiation supplying means in order to actively reduce a temperature gradient between the sensor means and the radiation supplying means and/or the at least one radiation detection device, thereby minimizing heat flux into the sensor means. For instance, a temperature of the at least one second heating device (and preferably of the at least one radiation supplying means and/or the at least one radiation detection device) may be adjusted using the second heating device to be essentially equal to a temperature sensed for instance at the first heat conducting means or at the patient's skin. Thereby, a temperature gradient across the optical sensor unit, in particular across the sensor means, in a perpendicular direction is minimized.

For sensing temperatures at various locations in the optical sensor unit, one or more temperature sensors provided at said various locations may be used. In particular, a first temperature sensor could be provided in the first heat conducting means at a position close to the skin, a second temperature sensor could be provided at the first heating device, and/or a third temperature sensor could be provided at the second heating device.

Preferably, the optical sensor unit is a transcutaneous sensor unit for measuring blood gas concentrations, in particular, gas concentrations of $O_2$ and/or $CO_2$. This application is advantageous, since it will enable to use transcutaneous gas monitoring at home without expensive patient's training or the presence of a trained nurse.

According to another aspect of the present invention, a method for measuring gas concentration is provided that uses an optical sensor unit as described above. The method preferably comprises the steps of receiving gas, which concentration is to be measured, in the at least one sensing layer after having passed the gas-permeable layer, irradiating the sensing layer with the predetermined radiation, and sensing the optical response of the at least one sensing layer, which depends on the gas concentration.

Even though the described embodiments will be explained in particular with reference to a transcutaneous non-invasive sensor for blood gas monitoring, the inventive sensor may be readily applied to different spheres in other systems as well, such as other blood gas sensors, sensors for wound care and home care products or in general to sensors for measuring gas concentrations.

BRIEF DESCRIPTION OF THE DRAWINGS

In the figures.

DETAILED DESCRIPTION OF THE EMBODIMENTS

The optical sensor unit according to the present invention may be a ready-to-use sensor plaster for measuring blood gas concentrations. The ready-to-use sensor plaster combines into a single plaster unit a sensor means (12, 13) that incorporates at least the sensing layer and the gas-permeable layer (membrane). The plaster unit may further comprise an adhesive layer (film). The plaster unit is packaged in an air and light tight package in such a way that the unit keeps its known response to $CO_2$ and/or $O_2$. After opening the package the plaster unit can be directly attached to a patient's skin, e.g. by using an adhesive layer provided at the optical sensor unit. The ready-to-use sensor plaster may be typically used for monitoring during one night but can also be used for monitoring during a couple of days. After removal of the sensor plaster from the skin, the sensor plaster may be disposed. Calibration is handled during manufacturing.

Figure 1:
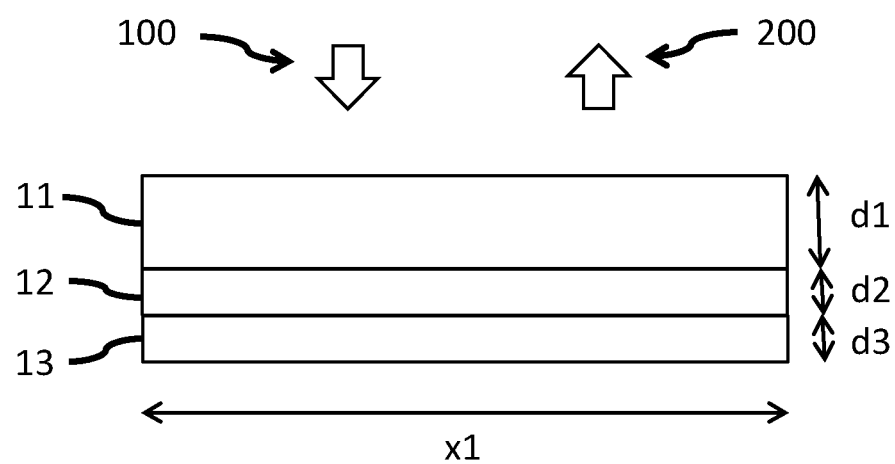
FIG. 1 shows a principle of operation of a chemo-optical sensor spot.
Figure 2:
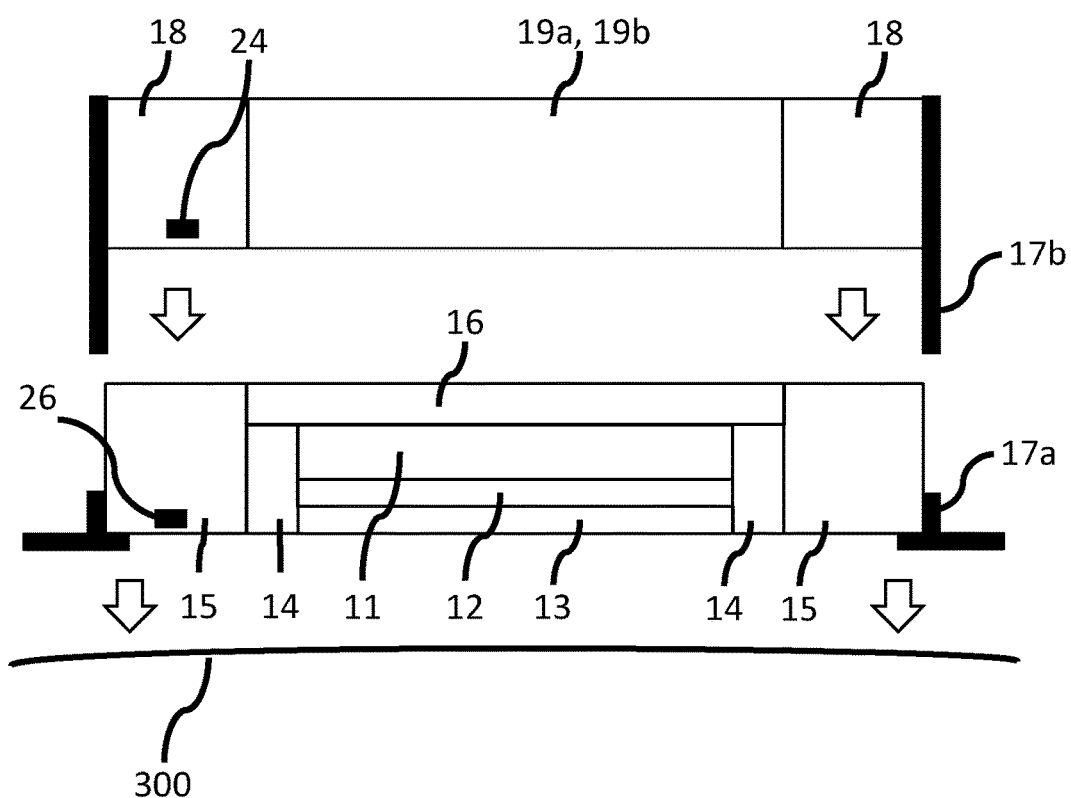
FIG. 2 shows a sectional view of an optical sensor unit according to a first embodiment of the present invention.

FIG. 2 shows a sectional view of an optical sensor unit 10 according to a first embodiment of the present invention. The optical sensor unit 10 may have a circular shape and may be attached to skin 300 of a patient. The optical sensor unit 10 comprises sensor means (12, 13) comprising a gas-permeable layer 13 and a sensing layer 12 overlying the gas-permeable layer 13. The gas-permeable layer 13 may be in contact with the skin 300, wherein preferably a contact fluid is provided between the skin and the gas-permeable layer 13 in order to ensure proper gas diffusion. An optical transparent layer 11 covers the sensing layer 12. First thermal insulation means 14 at least partially surround lateral sides of the optically transparent layer 11, the sensing layer 12 and/or the gas-permeable layer 13, in order to thermally isolate said layers from its environment. An interface layer 16 is provided to cover at least the optically transparent layer 11, and serves as optical coupling. The interface layer 16 has a high thermal resistance, and is, for instance, air. First heat conducting means 15 are provided to surround the sensor means (12, 13) and preferably also the interface layer 16, wherein the first heat conducting means 15 is in contact with the skin 300, either directly or via the above-mentioned contact fluid. The first heat conducting means 15 heats the skin, in order to increase blood perfusion and gas-permeability of the skin. Since the first heat conducting means 15 has a temperature higher than body temperature of 37° C., the first thermal insulation means 14 prevents heat from being introduced into the sensor means (12, 13).

A first support 17a is provided for supporting the sensor means (12, 13), interface layer 16 and/or first heat conducting means. A first unit comprising the sensor means (12, 13), first thermal insulation means 14, interface layer 16, first heat conducting means 15 and support 17a may be disposable. A second unit of the optical sensor unit comprising a second support 17b, a first heating device 18, radiation supplying means 19a and a radiation detection device 19b may be configured to be reusable. The first unit and the second unit may be connectable to and detachable from each other, e.g. using a clip-on mechanism.

The radiation supplying means 19a and the radiation detection device 19b may be adapted to be in contact with the interface layer 16 and to irradiate the predetermined radiation onto the sensing layer 12 and to receive, for instance, luminescent light from said sensing layer 12, respectively. The first heating device 18 may surround said radiation supplying means 19a and radiation detection device 19b, and may be in good thermal contact with the first heat conducting means 15. In particular, the first heating device 18 applies heat to the first heating conducting means 15, which heat is then used to heat the skin 300 to increase blood perfusion and gas permeability of the skin. The heating device 18 and the first heat conducting means 15 may have a circular shape, and may be made of metal having good thermal conductivity.

Temperature sensors 24, 26 may be provided to allow a control of the first heating device 18 based on sensed temperatures. Accordingly, a heat applied to the skin 300 may be controlled and adjusted. For instance, a temperature sensor 24 may be provided to measure a temperature of the first heating device 18, and a second temperature sensor 26 may be provided to measure a temperature of the first heat conducting means 15, preferably at a contact area of the optical sensor unit 10 to the skin 300. Accordingly, by said temperature measurements and by controlling the heat applied to the skin 300, the temperature at the skin sensor interface can be controlled and burns due to excessive heating can be avoided.

Figure 3:
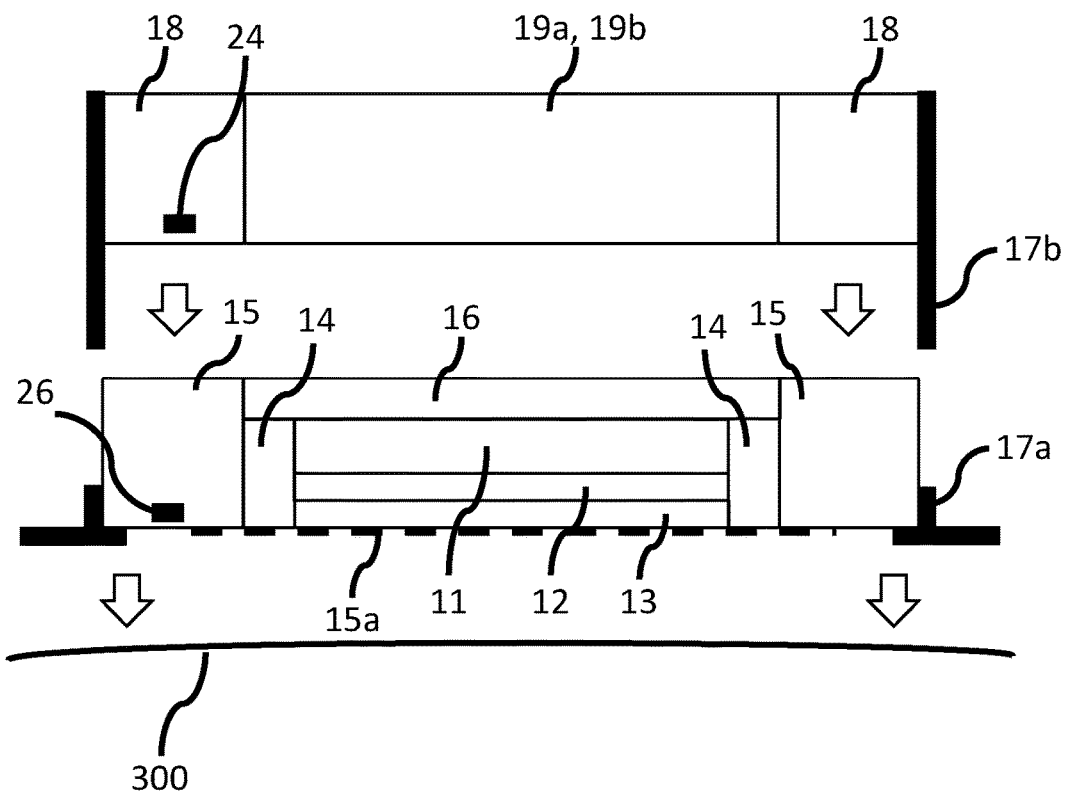
FIG. 3 shows a sectional view of an optical sensor unit according to a second embodiment of the present invention.

FIG. 3 shows a sectional view of an optical sensing unit 10 according to a second embodiment of the present invention. The second embodiment is similar to the first embodiment, and features already described with reference to the first embodiment are not repeated.

The optical sensor unit 10 according to the second embodiment further includes a portion 15a of the first heat conducting means 15 provided between the sensor means (12, 13), in particular the gas-permeable layer 13, and the skin 300. The portion 15a is perforated to allow gas exchange. In particular, the portion 15a may be a thin sheet of perforated metal. The metal may be the same metal the first conducting means 15 is made of. Accordingly, thermal gradients in the sensor means (12, 13) in a direction parallel to the gas-permeable layer/sensing layer are suppressed and a temperature of the sensor means is well-defined, thereby increasing accuracy of the gas concentration measurement.

Figure 4:
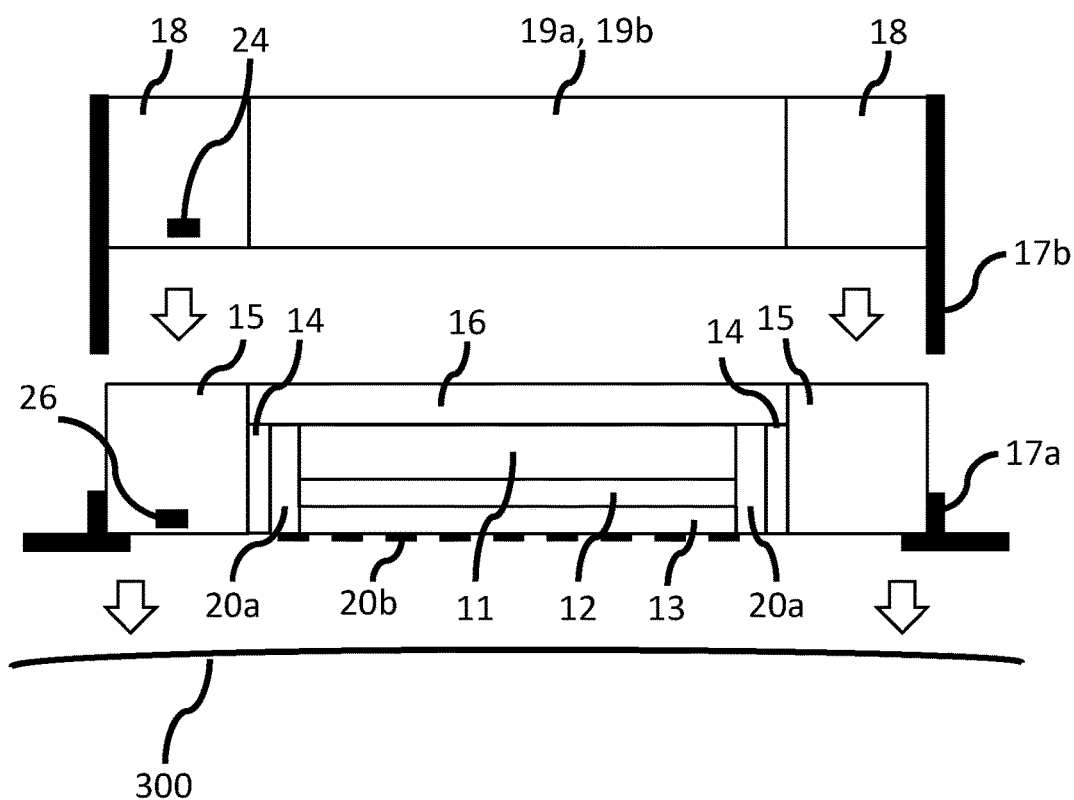
FIG. 4 shows a sectional view of an optical sensor unit according to a third embodiment of the present invention.

FIG. 4 shows a sectional view of an optical sensing unit 10 according to a third embodiment of the present invention. The third embodiment differs from the first embodiment shown in FIG. 2 in the provision of second heat conducting means 20a, 20b. The second heat conducting means 20a, 20b comprises an extending portion 20a interposed between the first thermal insulation means 14 and the sensor means (12, 13). The second heat conducting means 20a, 20b further comprises a portion 20b similar to the portion 15a shown in FIG. 3. The portion 20b may be perforated, and preferably, the portion 20b is a perforated thin metal sheet. By providing the second heat conducting means 20a, 20b, a uniform heat distribution in particular on an outer surface of the sensor means (12, 13) is ensured, thereby ensuring accuracy of the gas concentration measurement.

At least the portion 20b of the second heat conducting means 20a, 20b could be coated to be water repellant at the location of the sensor means (12, 13) to promote faster (for instance $CO_2$) gas transport. In an extreme case, the sensor means (12, 13) could be fully enclosed in a thermally conducting metal envelope, a chamber with only capillary excess holes for gas transmission and light transmission.

Figure 5:
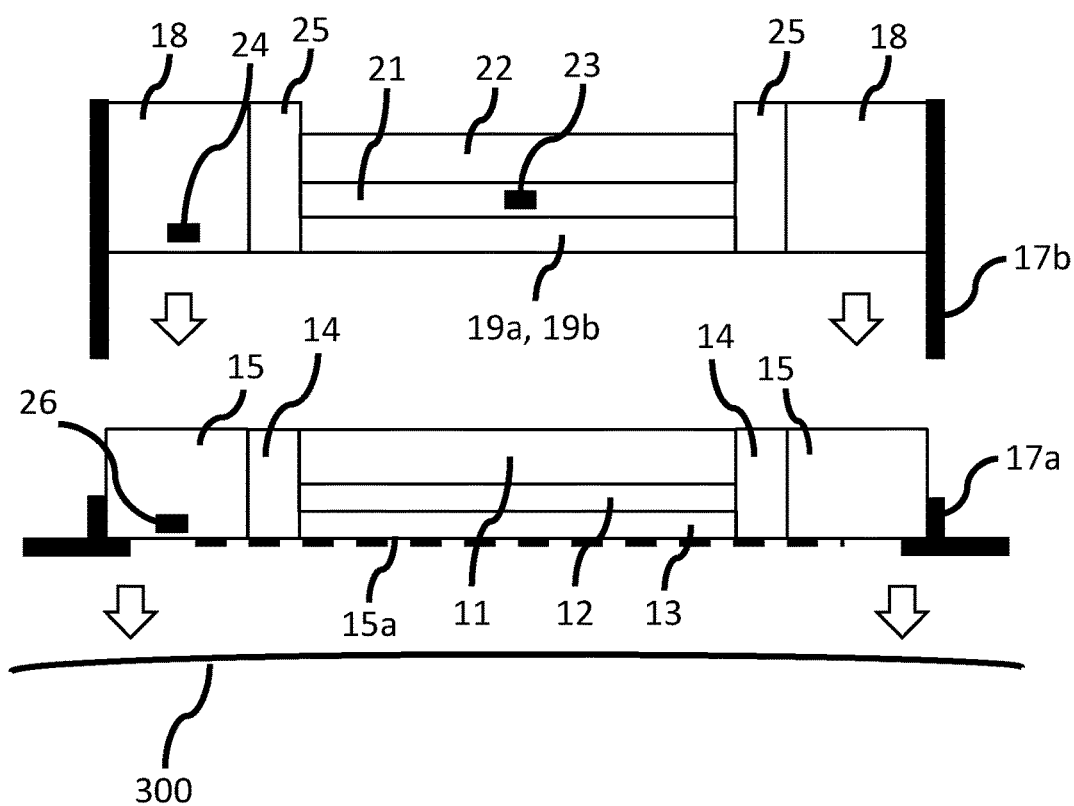
FIG. 5 shows a sectional view of an optical sensor unit according to a fourth embodiment of the present invention.

FIG. 5 shows a sectional view of an optical sensor unit 10 according to a fourth embodiment of the present invention. The sensor unit 10 of the fourth embodiment could be combined with the first to third embodiments. Moreover, the optical sensor unit 10 of the fourth embodiment further uses the above-mentioned zero heat flux method. For this purpose the optical sensor unit 10 further comprises a second heating device 22 and second thermal insulation means 25 provided in the re-usable unit. In particular, the second heating device 22 is provided on top of the radiation supplying means 19a and/or the radiation detection device 19b, wherein an additional layer 21 having a third temperature sensor 23 is provided there between. The second thermal insulation means 25 thermally isolates the radiation supplying means 19a, the radiation detection device 19b, the second heating device 22, and the intermediate layer 21 comprising the third temperature sensor 23 from the first heating device 18. In FIG. 5, no interface layer 16 is shown. However, the interface layer 16 could be provided as in the other embodiments.

The second heating device 22 may be used in an active zero heat flux (ZHF) method. In this method, thermal flux into the sensor means (12, 13) is actively reduced by minimizing a temperature gradient across a thermal resistance (in particular the sensor means (12, 13)). For instance, by heating the second heating device 22, the radiation supplying means 19a and the radiation detection device 19b, e.g. to a temperature essentially identical to a temperature measured at the skin 300 by means of the second temperature sensor 26, a temperature gradient across the sensor means (12, 13) is reduced and heat is prevented from flowing into the sensor means (12, 13).

Figure 6:
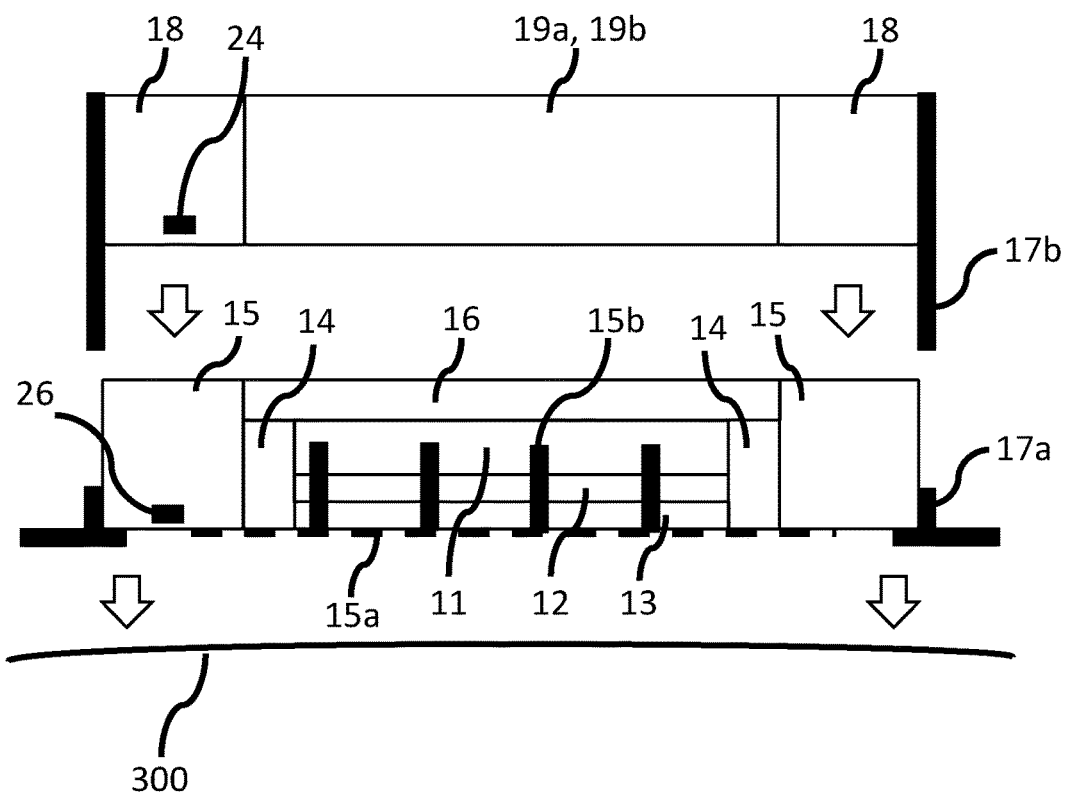
FIG. 6 shows a sectional view of an optical sensor unit according to a fifth embodiment of the present invention.

FIG. 6 shows a sectional view of an optical sensor unit 10 according to a fifth embodiment of the present invention. The fifth embodiment of the present invention could be combined with the second to fourth embodiments, wherein further at least one extension part 15b, preferably column-shaped, is provided to extend into the sensor means. The extension part 15b may extend from the first heat conducting means 15 (the second heat conducting means 20a, 20b in the third embodiment) and may extend from the portion 15a (portion 20a in the third embodiment) of said first heat conducting means 15 covering the side of the at least one gas-permeable layer 13. More than one extension parts 15b could be provided. The extension parts 15b are implemented as heat conducting bodies in order to minimize a thermal resistance in the sensor means. The extension part 15b may penetrate at least partially into the gas-permeable layer 13, and may further penetrate at least partially into the sensing layer 12, too. Although not shown, a plurality of extension parts 15b could have different heights and/or diameters.

Figure 7:
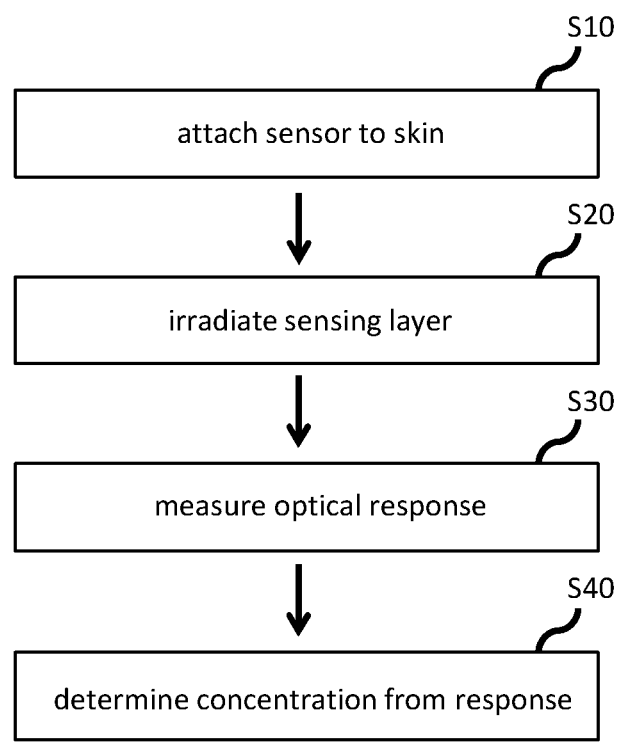
FIG. 7 shows a flow diagram of a method for measuring a gas concentration using an optical sensor according to the present invention.

FIG. 7 shows a flow diagram of a method for measuring a gas concentration using an optical sensor unit 10 according to the present invention. In step S10, the optical sensor unit 10 is attached to skin 300 of a patient. The gas-permeable layer 13 contacts the skin, either directly or via a contact medium (e.g. gel). An adhesive layer could be provided to firmly attach the optical sensor unit 10 to the skin 300 and to shield the gas-permeable layer 12 from surrounding air. After attaching the optical sensor unit 10, the first heating device 18 may be used to heat the skin 300 underlying the optical sensor unit 10 in order to increase capillary blood flow and bring the capillary blood gas levels close to the arterial blood gas levels. Gas, which leaves the skin 300, passes the gas-permeable layer 13 providing a predetermined diffusible rate and reaches the sensing layer 12. In step S20, the sensing layer 12 is irradiated with predetermined radiation, which is preferably visible light, infrared light or UV-radiation. Irradiating the sensing layer 12 causes the sensing layer 12 to generate luminescent light, the intensity of which depends on the amount of gas having diffused into the sensing layer 12. In particular, the intensity of the luminescent light varies according to the concentration of the gas in the sensing layer 12. In step S30 the optical response, i.e. an intensity of the luminescent light, is measured/sensed by the radiation detection device 19b. In step S40, the gas concentration in the sensing layer is determined from the measured/sensed optical response, wherein arterial blood gas levels could then be derived from the determined gas concentration in the sensing layer.

The present invention provides thermal insulation of the sensor means from its environment and/or an active reduction of a thermal flux into the sensor means and/or a reduction of a thermal resistance of the sensor means. Accordingly, temperature gradients, for instance in a direction perpendicular and/or parallel to a sensing layer and/or a gas-permeable layer included in the sensor means, can be minimized or even eliminated, thereby preventing the gradient-dependent signal drift (thermal creep/thermal transpiration) associated with the prior art. Furthermore, by suppressing temperature gradients, temperature effects on the exited states and chemical balances inside the sensing layer (for instance a dye) are avoided, and hence, luminescence changes due to temperature are suppressed. This significantly increases reliability and accuracy of the gas concentration measurement.

The invention claimed is:

1. An optical sensor unit for measuring gas concentration, comprising:
sensor means, including:
at least one sensing layer adapted to be irradiated with a predetermined radiation; and
at least one gas-permeable layer adjacent to one side of the at least one sensing layer and configured to pass gas through the gas-permeable layer towards the at least one sensing layer; and
at least one first heating device;
first thermal insulation means at least partially surrounding the sensor means and positioned between the sensor means and the at least one first heating device, the first thermal insulation means configured to insulate the sensor means from heat generated by the at least one heating device; and
a radiation detector configured to detect an optical response of the at least one sensing layer to the predetermined radiation, and determine gas concentration of the gas passed through the gas-permeable layer towards the at least one sensing layer, based on the optical response.

2. The optical sensor unit of claim 1, further comprising at least one first heat conducting means, the at least one first heat conducting means at least partially surrounding the sensor means and/or the first thermal insulation means, the at least one first heat conducting means configured to apply heat to a skin of a subject.

3. The optical sensor unit of claim 2, wherein the at least one first heating device providing heat to the at least one first heat conducting means, wherein the at least one first heating device is configured to be detachably connected to the optical sensor unit.

4. The optical sensor unit of claim 1, further comprising: at least one radiation supplying means adapted to irradiate the at least one sensing layer with the predetermined radiation, wherein the at least one radiation supplying means and/or the radiation detector are configured to be detachably connected to the optical sensor unit.

5. The optical sensor unit of claim 2, wherein the at least one first heat conducting means is configured to partially cover a side of the at least one gas-permeable layer opposite the at least one sensing layer.

6. The optical sensor unit of claim 5, wherein at least a portion of the at least one first heat conducting means covering the side of the at least one gas-permeable layer has perforations formed therein.

7. The optical sensor unit of claim 2, wherein the at least one first heat conducting means comprises at least one extension part at least partially extending into the sensor means.

8. The optical sensor unit of claim 2, further comprising a second heat conducting means configured to at least partially cover a side of the at least one gas-permeable layer opposite the at least one sensing layer while being thermally insulated from the at least one first heat conducting means.

9. The optical sensor unit of claim 8, wherein at least a portion of the second heat conducting means covering the side of the at least one gas-permeable layer has perforations formed therein.

10. The optical sensor unit of claim 8, wherein the second heat conducting means comprises an extending portion extending at least partially between the sensor means and the first thermal insulation means.

11. The optical sensor unit of claim 8, wherein the second heat conducting means comprises at least one extension part at least partially extending into the sensor means.

12. The optical sensor unit of claim 3, further comprising a second thermal insulation means configured to thermally isolate the first heating device from the at least one radiation supplying means and/or the radiation detector.

13. The optical sensor unit of claim 12, further comprising at least one second heating device configured to heat the at least one radiation supplying means and/or the radiation detector, while being thermally isolated from the at least one first heating device by the second thermal insulation means, wherein the at least one second heating device is configured to perform a zero heat flux method.

14. The optical sensor unit of claim 1, wherein the optical sensor unit is a transcutaneous sensor unit for measuring blood gas concentration, in particular gas concentration of $O_2$ and/or $CO_2$.

15. A method for measuring gas concentration using the optical sensor unit of claim 1, the method comprising:
receiving gas, whose concentration is to be measured, in the at least one sensing layer after having passed the at least one gas-permeable layer;
irradiating the at least one sensing layer with the predetermined radiation; and
sensing the optical response of the at least one sensing layer; and determining the gas concentration based on the optical response.

16. An optical sensor unit for measuring gas concentration, comprising:
   a sensor, including:
      at least one sensing layer adapted to be irradiated with a predetermined radiation; and
      at least one gas-permeable layer adjacent to one side of the at least one sensing layer and configured to pass gas through the at least one gas-permeable layer towards the sensing layer; and
   at least one first heating device;
   a first thermal insulator at least partially surrounding the sensor and positioned between the sensor and the at least one first heating device, the first thermal insulator configured to insulate the sensor from heat generated by the at least one heating device; and
   a radiation detector configured to detect an optical response of the sensing layer to the predetermined radiation, and determine gas concentration of the gas passed through the at least one gas-permeable layer towards the at least one sensing layer, based on the optical response.

17. The optical sensor unit of claim 16, further comprising at least one first heat conductor, the at least one first heat conductor at least partially surrounding the sensor and/or the first thermal insulator, the at least one first heat conductor configured to apply heat to a skin of a subject.

18. The optical sensor unit of claim 17, wherein the at least one first heating device providing heat to the at least one first heat conductor, and wherein the at least one first heating device is configured to be detachably connected to the optical sensor unit.

19. The optical sensor unit of claim 16, further comprising: at least one radiator adapted to irradiate the at least one sensing layer with the predetermined radiation, and wherein the at least one radiator and/or the radiation detector are configured to be detachably connected to the optical sensor unit.

20. The optical sensor unit of claim 17, wherein the first heat conductor is configured to partially cover a side of the at least one gas-permeable layer opposite the at least one sensing layer.

* * * * *